United States Patent [19]
Patton et al.

[11] Patent Number: 6,153,776
[45] Date of Patent: Nov. 28, 2000

[54] BIMETALLIC COMPLEXES AND POLYMERIZATION CATALYSTS THEREFROM

[75] Inventors: Jasson T. Patton, Midland, Mich.; Tobin J. Marks; Liting Li, both of Evanston, Ill.

[73] Assignee: The Dow Chemical, Midland, Mich.

[21] Appl. No.: 09/141,659

[22] Filed: Aug. 28, 1998

Related U.S. Application Data

[60] Provisional application No. 60/060,712, Sep. 15, 1997, and provisional application No. 60/092,294, Jul. 10, 1998.

[51] Int. Cl.$^7$ .............................. C07F 17/00; C07F 7/00; C08F 4/44
[52] U.S. Cl. ................................ 556/11; 556/1; 556/12; 556/21; 556/28; 556/43; 556/53; 556/58; 548/402; 534/15; 526/126; 526/160; 526/352; 526/943; 502/103; 502/117; 502/152; 502/155
[58] Field of Search ................................ 556/7, 11, 12, 556/21, 28, 1, 43, 53, 58; 502/103, 117, 152, 155; 534/15; 526/126, 160, 352, 943, 113; 548/402

[56] References Cited

U.S. PATENT DOCUMENTS

| | | | |
|---|---|---|---|
| 3,242,099 | 3/1966 | Manyik et al. | 252/429 |
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,198,401 | 3/1993 | Turner et al. | 502/155 |
| 5,372,980 | 12/1994 | Davis | 502/103 |
| 5,374,696 | 12/1994 | Rosen et al. | 526/126 |
| 5,470,993 | 11/1995 | Devore et al. | 556/11 |

FOREIGN PATENT DOCUMENTS

| | | |
|---|---|---|
| 0779295 | 6/1987 | European Pat. Off. . |
| 416815 | 7/1990 | European Pat. Off. . |
| 0739897 | 10/1996 | European Pat. Off. . |

OTHER PUBLICATIONS

Chemical Abstract, vol. 120, No. 3, Jan. 17, 1994 Abstract No. 30861v, Elschenbroich, et al.

Organomet. Chem., 460, 191 (1993).

*Primary Examiner*—Porfirio Nazario-Gonzalez

[57] ABSTRACT

Group 3–6 or Lanthanide metal complexes possessing two metal centers, catalysts derived therefrom by combining the same with strong Lewis acids, Bronsted acid salts, salts containing a cationic oxidizing agent or subjected to bulk electrolysis in the presence of compatible, inert non-coordinating anions and the use of such catalysts for polymerizing olefins, diolefins and/or acetylenically unsaturated monomers are disclosed.

9 Claims, No Drawings

BIMETALLIC COMPLEXES AND POLYMERIZATION CATALYSTS THEREFROM

BENEFIT OF PRIOR APPLICATION

This application claims benefit of priority from Provisional application Ser. No. 60/060712, filed Sep. 15,1997 and from a Provisional application Ser. No. 60/092294, filed Jul. 10, 1998.

GOVERNMENTAL INTEREST

The United States Government has rights in this invention pursuant to funding of research by the United States Department of Energy pursuant to Grant No. 86-ER13511.

BACKGROUND OF THE INVENTION

This invention relates to certain Group 3, 4 or Lanthanide metal complexes possessing two metal centers and to polymerization catalysts obtained therefrom. In one form this invention relates to such metal complexes per se. In another embodiment of the claimed invention, the complexes can be activated to form catalysts for the polymerization of olefins. Also included in the invention are processes for preparing such complexes and methods of using the catalysts in addition polymerizations.

Biscyclopentadienyl Group 4 transition metal complexes in which the metal is in the +4, +3 or +2 formal oxidation state, and olefin polymerization catalysts formed from such by combination with an activating agent, for example, alumoxane or ammonium borate, are well known in the art. Thus, U.S. Pat. No. 3,242,099 describes the formation of olefin polymerization catalysts by the combination of biscyclopentadienyl metal dihalides with alumoxane. U.S. Pat. No. 5,198,401 discloses tetravalent biscyclopentadienyl Group 4 transition metal complexes and olefin polymerization catalysts obtained by converting such complexes into cationic forms in combination with a non-coordinating anion. Particularly preferred catalysts are obtained by the combination of ammonium borate salts with the biscyclopentadienyl titanium, zirconium or hafnium complexes. Among the many suitable complexes disclosed are bis (cyclopentadienyl)zirconium complexes containing a diene ligand attached to the transition metal through σ-bonds where the transition metal is in its highest formal oxidation state. R. Mülhaupt, et al., *J. Organomet. Chem.*, 460, 191 (1993), reported on the use of certain binuclear zirconocene derivatives of dicyclopentadienyl-1,4-benzene as catalysts for propylene polymerization.

Constrained geometry metal complexes, including titanium complexes, and methods for their preparation are disclosed in U.S. application Ser. No. 545,403, filed Jul. 3,1990 (EP-A-416,815); U.S. Pat. Nos. 5,064,802, 5,374, 696, 5,055,438, 5,057,475, 5,096,867, and U.S. Pat. No. 5,470,993.

Metal complexes of the constrained geometry type containing two metal centers joined by means of a dianionic ligand separate from and unconnected to the ligand groups in such complexes that contain delocalized π-electrons, are previously taught, but not exemplified, in U.S. Pat. No. 5,055,438.

SUMMARY OF THE INVENTION

The present invention relates to bimetallic complexes corresponding to the formula:

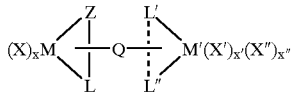

(I)

wherein:

M and M' are independently Group 3, 4, 5, 6, or Lanthanide metals;

L is a divalent group (or trivalent group if bound to Q) having up to 50 nonhydrogen atoms and containing an aromatic π-system through which the group is bound to M, said L also being bound to Z;

L' is a monovalent group or a divalent group (if bound to L" or Q), or a trivalent group if bound to both L" and Q) having up to 50 nonhydrogen atoms and containing an aromatic π-system through which the group is bound to M';

L" is a monovalent group or a divalent group (if bound to L' or Q), or a trivalent group if bound to both L' and Q) having up to 50 nonhydrogen atoms and containing an aromatic π-system through which the group is bound to M', or L" is a moiety comprising boron or a member of Group 14 of the Periodic Table of the Elements, and optionally also comprising nitrogen, phosphorus, sulfur or oxygen, said L" having up to 20 non-hydrogen atoms;

Z is a moiety comprising boron or a member of Group 14 of the Periodic Table of the Elements, and optionally also comprising nitrogen, phosphorus, sulfur or oxygen, said Z having up to 20 non-hydrogen atoms;

X and X' independently each occurrence are anionic ligand groups having up to 40 atoms exclusive of the class of ligands containing an aromatic 7-system through which the group is bound to M or M', or optionally two X groups or two X' groups together form a $C_{4-40}$ conjugated or nonconjugated diene optionally substituted with one or more hydrocarbyl, silyl, halocarbyl, or halohydrocarbyl groups;

X" independently each occurrence is a neutral ligating compound having up to 20 atoms;

Q is a divalent anionic ligand group bound at one terminus to either Z or L and bound at the remaining terminus to either L' or L", said Q having up to 20 nonhydrogen atoms;

x and x' are independently integers from 0 to 3, selected to provide charge balance; and x" is a number from 0 to 3.

Additionally according to the present invention there is provided a composition of matter useful as an addition polymerization catalyst comprising:

1) at least one bimetallic complex (I) as previously disclosed, and 2) one or more activating cocatalysts, the molar ratio of 1) to 2) being from 1:10,000 to 100:1, or the reaction product formed by converting 1) to an active catalyst by use of an activating technique.

Further additionally according to the present invention there is provided a process for polymerization of one or more addition polymerizable monomers comprising contacting said monomer or a mixture of said monomers with a catalyst comprising the aforementioned composition of matter.

Finally, the present invention also relates to novel methods of preparing the complexes including the following schematic reaction:

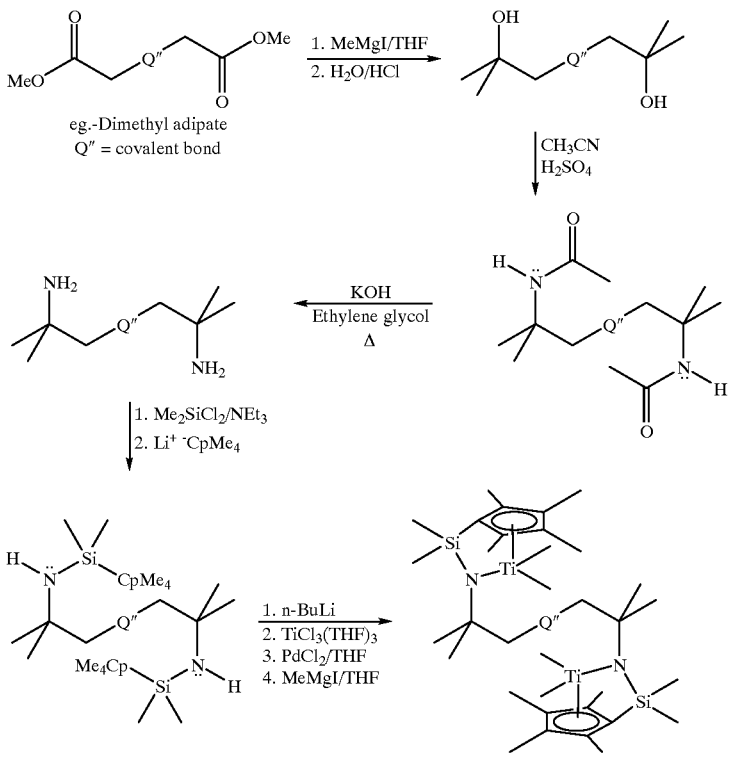

The invented catalyst compositions allow the preparation of mixtures of polymers from a single monomer or mixture of monomers thereby forming directly a polymer blend in the reactor. This result is accentuated where different metals, different metal valencies or different ligand groups attached to the two metal centers are employed. Alternatively, the invention allows for increased incorporation of long chain branching in a polymer formed from a single monomer, especially ethylene, or a mixture of monomers, due to selection of one metal center adapted to forming oligomeric products terminated by vinyl functionality in combination with a second metal center adapted to form high molecular weight polymers or adapted to long chain α-olefin incorporation into a polymer.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Preferred metal coordination complexes according to the present invention correspond to the following formulas:

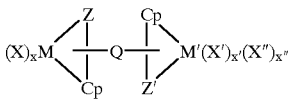

wherein Z, M, M', X, X', x and x' are as previously defined;

Z' is a moiety comprising boron or a member of Group 14 of the Periodic Table of the Elements, and optionally also comprising nitrogen, phosphorus, sulfur or oxygen, said Z' having up to 20 non-hydrogen atoms;

Cp and Cp' are cyclic $C_5R'_4$ groups bound to Z or Z' respectively and bound to M or M' respectively by means of delocalized π-electrons, wherein R', independently each occurrence, is hydrogen, hydrocarbyl, silyl, halo, fluorohydrocarbyl, hydrocarbyloxy, hydrocarbylsiloxy, N,N-di(hydrocarbylsilyl)amino, N-hydrocarbyl-N-silylamino, N,N-di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two such R' substituents may be joined together thereby causing Cp or Cp' to have a fused ring structure, or further optionally, Cp or Cp' each independently is a trivalent derivative of the above identified $C_5R'_4$ group that is also bonded to Q and one R' on each of Cp or Cp' is a covalent bond to Q;

Q is a linear or cyclic hydrocarbylene, or silane group or a nitrogen, oxygen, or halo substituted derivative thereof, said Q having up to 20 nonhydrogen atoms.

More preferred metal coordination complexes according to the present invention correspond to the formula:

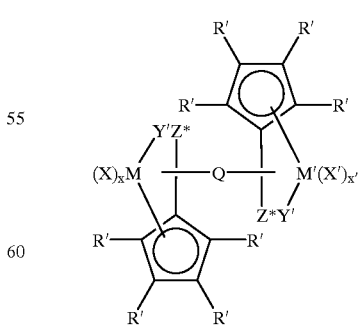

wherein:

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

Z and Z' independently each occurrence are —Z*Y'—, wherein:

Y' is —O—, —S—, —NR"—, —PR"—, —OR", or —NR"$_2$ (and with respect to —OR" and —NR"$_2$, one bond is a dative bond through the available electron pair), wherein R" is hydrogen, hydrocarbyl, silyl, or silylhydrocarbyl of up to 12 nonhydrogen atoms, or R" is a covalent bond to Q, and Z* is SiR*$_2$, CR*$_2$, SiR*$_2$SiR*$_2$, CR*$_2$CR*$_2$, CR*=CR*, CR*$_2$SiR*$_2$, or GeR*$_2$;

wherein R* each occurrence is independently hydrogen, hydrocarbyl, silyl, halogenated alkyl, or halogenated aryl, said R* having up to 12 non-hydrogen atoms.

More highly preferred metal coordination complexes are amidosilane- or amidoalkanediyl-compounds corresponding to the formula:

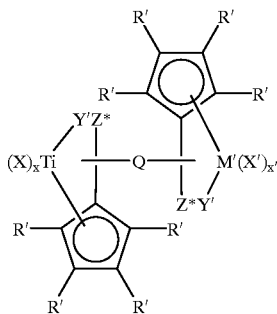

wherein:

Q is a linear or cyclic hydrocarbylene, silane group or a nitrogen or oxygen containing derivative thereof, M' is Ti, Zr, Hf, Sc, yittrium, or La;

R' is as previously defined;

X and X' are C$_{1-10}$ hydrocarbyl; and

Y'Z* is: —NR"—(ER'")$_m$— wherein:

E is independently each occurrence silicon or carbon;

R" is C$_{1-10}$ hydrocarbyl or a covalent bond to 0;

R'" is C$_{1-4}$ alkyl; and m is an integer from 1 to 10.

Preferably, R' independently each occurrence is hydrogen, hydrocarbyl, silyl, fluorophenyl, hydrocarbyloxy, N,N-di(hydrocarbyl)amino, hydrocarbyleneamino, or hydrocarbyloxy-substituted hydrocarbyl, said R' having up to 20 non-hydrogen atoms, or two adjacent R' groups are joined together forming part of a fused ring system. Most preferably, R' is hydrogen, methyl, ethyl, propyl, butyl, pentyl, hexyl, (including where appropriate all isomers), cyclopentyl, cyclohexyl, norbornyl, benzyl, phenyl, N,N-di(methyl)amino, pyrrolyl, pyrrolidinyl, or two R' groups are linked together, the entire C$_5$R'$_4$ group thereby forming an indenyl, tetrahydroindenyl, fluorenyl, tetrahydrofluorenyl, indacenyl, or octahydrofluorenyl group, or a C$_{1-6}$ hydrocarbyl-substituted, N,N-di(methyl)amino-substituted, or pyrrolyl-substituted derivative thereof.

Examples of suitable X or X' groups for all of the foregoing structural depictions of the invention include single atomic groups including hydride or halide, as well as multi-atomic groups such as hydrocarbyl, hydrocarbyloxy, dihydrocarbylamido (including cyclic hydrocarbyleneamido groups) and halo, amino, or phosphino substituted derivatives thereof, said multi-atomic groups containing up to 20 nonhydrogen atoms. Specific examples include chloride, methyl, benzyl, allyl, N,N-dimethylamido, pyrrolinado, pyrrolidinado, (N,N-dimethylamino)benzyl, phenyl, methoxide, ethoxide, isopropoxide and isobutoxide. Most preferably X and X' are chloride, methyl, N,N-dimethylamido, or benzyl.

In the embodiments wherein two X or wherein two X' groups together form a diene group or substituted diene group, such group may form a π-complex with M or M' or the diene may form a σ-complex with M or M'. In such complexes M and M' are preferably Group 4 metals, most preferably Ti. In such complexes in which the diene is associated with the metal as a σ-complex, the metal is in the +4 formal oxidation state and the diene and metal together form a metallocyclopentene. In such complexes in which the diene is associated with the metal as a π-complex, the metal is in the +2 formal oxidation state, and the diene normally assumes a s-trans configuration or an s-cis configuration in which the bond lengths between the metal and the four carbon atoms of the conjugated diene are nearly equal. The dienes of complexes wherein the metal is in the +2 formal oxidation state are coordinated via π-complexation through the diene double bonds and not through a metallocycle resonance form containing σ-bonds. The nature of the bond is readily determined by X-ray crystallography or by NMR spectral characterization according to the techniques of Yasuda, et al., *Organometallics,* 1, 388 (1982), (Yasuda I); Yasuda, et al. *Acc. Chem. Res.,* 18, 120 (1985), (Yasuda I); Erker, et al., *Adv. Organomet. Chem.,* 24, 1 (1985)(Erker, et al. (I)); and U.S. Pat. No. 5,198,401. By the term "π-complex" is meant both the donation and back acceptance of electron density by the ligand are accomplished using ligand π-orbitals. Such dienes are referred to as being π-bound. It is to be understood that the present complexes may be formed and utilized as mixtures of the π-complexed and σ-complexed diene compounds.

The formation of the diene complex in either the π or σ state depends on the choice of the diene, the specific metal complex and the reaction conditions employed in the preparation of the complex. Generally, terminally substituted dienes favor formation of π-complexes and internally substituted dienes favor formation of σ-complexes. Especially useful dienes for such complexes are compounds that do not decompose under reaction conditions used to prepare the complexes of the invention. Under subsequent polymerization conditions, or in the formation of catalytic derivatives of the present complexes, the diene group may undergo chemical reactions or be replaced by another ligand.

Examples of suitable dienes (two X or X' groups taken together) include:

butadiene, 1,3-pentadiene, 1,3-hexadiene, 2,4-hexadiene, 1,4-diphenyl-1,3-butadiene, 3-methyl-1,3-pentadiene, 1,4-dibenzyl-1,3-butadiene, 1,4-ditolyl-1,3-butadiene, and 1,4-bis(trimethylsilyl)-1,3-butadiene.

Examples of the preferred metal complexes according to the present invention include compounds wherein R" is methyl, ethyl, propyl, butyl, pentyl, hexyl, (including all isomers of the foregoing where applicable), cyclododecyl, norbornyl, benzyl, phenyl, or a covalent bond to Q; Q is 1,2-ethylene or silane, and the cyclic delocalized π-bonded group is cyclopentadienyl, tetramethylcyclopentadienyl, indenyl, tetrahydroindenyl, 2-methylindenyl, 2,3-dimethylindenyl, 2-methyl-4-phenylindenyl, 3-N,N-dimethylaminoindenyl, 3-(pyrrolyl)inden-1-yl, 3-(pyrrolidinyl)inden-1-yl, fluorenyl, tetrahydrofluorenyl, indacenyl or octahydrofluorenyl group; M is titanium in the +2 or +4 formal oxidation state; M' is scandium in the +3 formal oxidation state, titanium in the +2, +3 or +4 formal oxidation state, or zirconium in the +4 formal oxidation state.

Examples of the foregoing metal complexes include all of the following (where methyl groups are represented by line segments and ( )$_n$ indicates a $C_{1-20}$ hydrocarbylene bridging group):

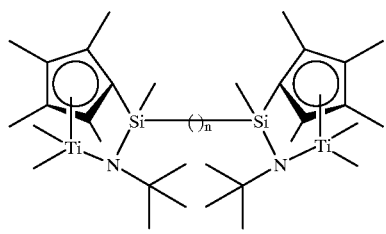

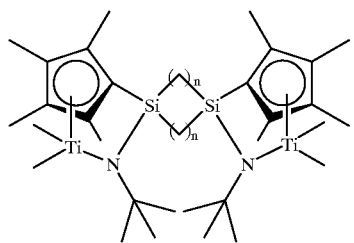

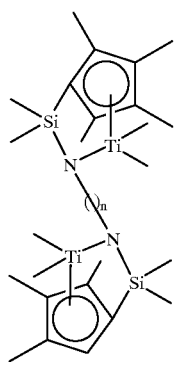

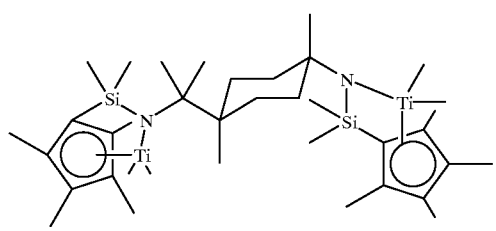

-continued

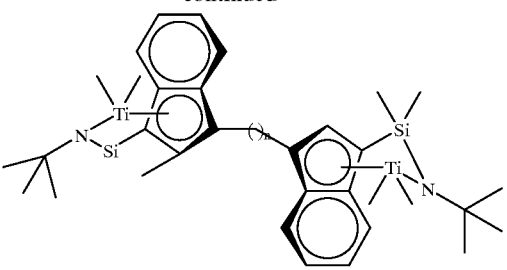

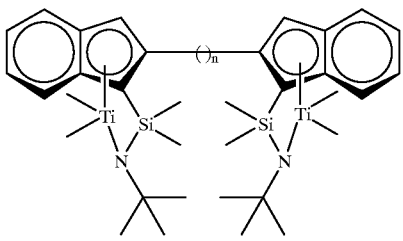

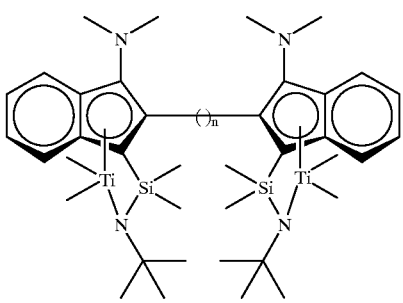

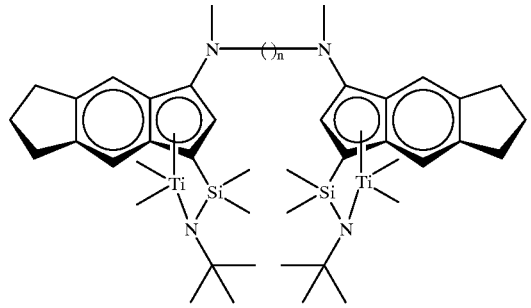

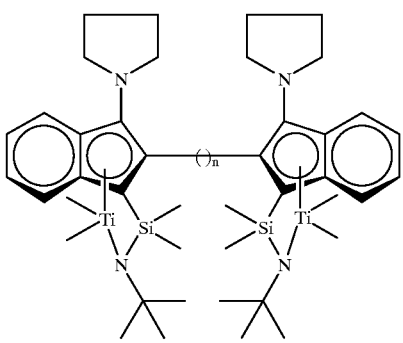

-continued

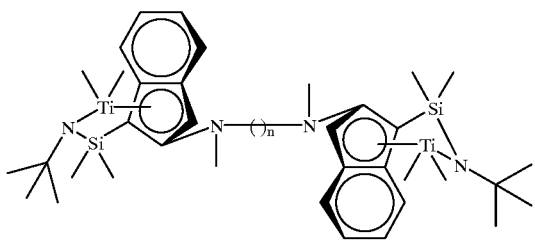

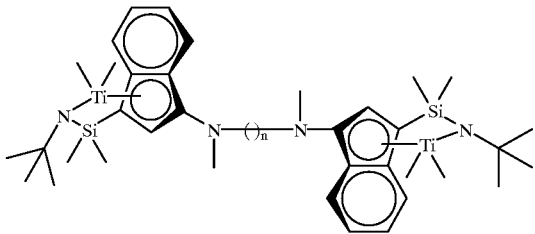

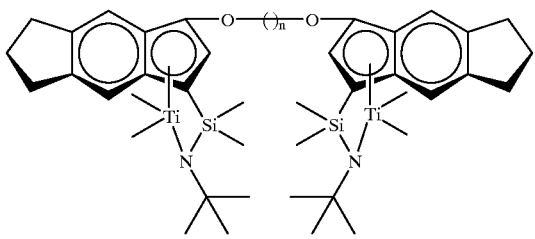

and

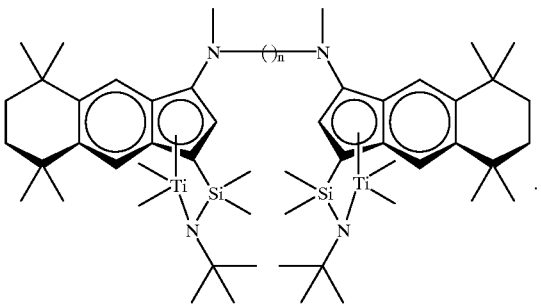

More preferred still according to the invention are zirconium and titanium bimetallic complexes corresponding to the formula:

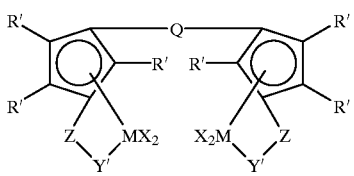

(II)

wherein:

M independently each occurrence is titanium or zirconium;

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, Z independently each occurrence is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$; wherein $R^*$ each occurrence is independently hydrogen, hydrocarbyl, silyl, halogenated alkyl, or halogenated aryl, said $R^*$ having up to 12 non-hydrogen atoms;

Y' is —O—, —S—, —NR"—, or —PR, wherein R" is hydrogen, hydrocarbyl, silyl, or silylhydrocarbyl of up to 12 nonhydrogen atoms; and X independently each occurrence is an anionic ligand group having up to 40 atoms exclusive of the class of ligands containing an aromatic π-system through which the group is bound to M, or optionally two X groups together form a $C_{4-40}$ conjugated or nonconjugated diene optionally substituted with one or more hydrocarbyl, silyl, halocarbyl, or halohydrocarbyl groups; and Q is a divalent anionic ligand group having up to 20 nonhydrogen atoms.

Especially preferred metal coordination complexes correspond to the forgoing formula 11, wherein Q is a linear or cyclic hydrocarbylene or silane group of up to 20 atoms other than hydrogen;

R' is hydrogen, $C_{1-20}$ hydrocarbyl, or two adjacent R' groups are joined together forming part of a fused ring system;

X is chloride, NR"$_2$, or R"; wherein R" is $C_{1-10}$ hydrocarbyl; and

Y'Z is: —NR"—(ER'")$_m$— wherein:

E is independently each occurrence silicon or carbon;

R" is $C_{1-10}$ hydrocarbyl;

R'" is $C_{1-4}$ alkyl; and m is an integer from 1 to 10.

Even more further preferred metal coordination complexes according to the present invention correspond to the forgoing formula II, wherein M in both occurrences is titanium or zirconium;

Q is a 1,2-ethanediyl;

the unsaturated ring system is cyclopentadienyl or indenyl;

X is chloride, N,N-dimethylamido or methyl; and

Y'Z is: dimethyl(t-butylamido)silane.

Examples of the foregoing more further preferred bimetallic complexes include: zirconium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis-, zirconium, dimethyl(N-(1,1-dimethylethyl)-1-((1,2,3,3a,7a-η)-1H-inden-1-yl)-1,1-dimethylsilanaminato(2-)-N)(3,3'-(1,2-ethanediyl)bis-, titanium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis-, or titanium, dimethyl(N-(1,1-dimethylethyl)-1-((1,2,3,3a,7a-η)-1H-inden-1-yl)-1,1-dimethylsilanaminato(2-)-N)(3,3'-(1,2-ethanediyl)bis-. Such complexes are of the formula:

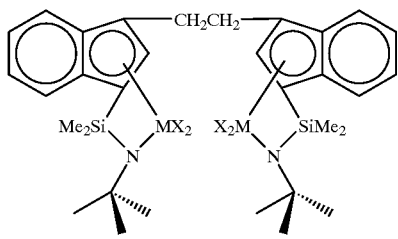

wherein M is titanium or zirconium and X is methyl or dimethylamido.

In general, the complexes of the present invention can be prepared by combining the dimetallated or diGrignard compound derived from the group Q in the resulting complex, with the precursor complex or mixture of complexes in a suitable noninterfering solvent at a temperature from −100° C. to 300° C., preferably from −78 to 130° C., most preferably from −10 to 120° C. More particularly, the complexes can be prepared by lithiating a compound of the formula HCp—Q—CpH, such as 1,2-ethane (bisinden-1-yl), reacting the resulting dimetallated compound with excess dimethyldichlorosilane, followed by 2 equivalents of t-butylamine, and reacting the resulting product with a titanium or zirconium tetrachloride salt. The corresponding hydrocarbyl or diene derivative may be prepared by known exchange with the metal hydrocarbyl or conjugated diene under reducing conditions. Alternatively, the desired bimetal dihydrocarbyl complex can be directly formed by reaction with a titanium or zirconium tetraamide, especially titanium tetra(N,N-dimethylamide) or zirconium tetra(N,N-dimethylamide), under ring formation conditions, followed by reaction with excess aluminum trialkyl to form the desired dialkyl derivative. Modifications of the foregoing preparation procedure to prepare alternative compound of the invention may be employed by the skilled artisan without departing from the scope of the present invention.

Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and , $C_{1-4}$ dialkyl ethers, $C_{1-4}$ dialkyl ether derivatives of (poly)alkylene glycols, and tetrahydrofuran. Mixtures of the foregoing list of suitable solvents are also suitable.

The recovery procedure involves separation of the resulting alkali metal or alkaline earth metal salt and devolatilization of the reaction medium. Extraction into a secondary solvent may be employed if desired. Alternatively, if the desired product is an insoluble precipitate, filtration or other separation technique may be employed.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids (the term "strong" as used herein defines Lewis acids which are not Bronsted acids), such as $C_{1-30}$ hydrocarbyl substituted Group 13 compounds, especially tri (hydrocarbyl)aluminum- or tri(hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris(pentafluorophenyl) borane or 1,4-tetrafluorophenylene bis{bis (pentafluorophenyl)borane}; nonpolymeric, ionic, compatible, noncoordinating, activating compounds (including the use of such compounds under oxidizing conditions); and combinations thereof. The foregoing activating cocatalysts and activating techniques have been previously taught with respect to different metal complexes in the following references: EP-A-277,003, U.S. Pat Nos. 5,153,157, 5,064,802, 5,321,106, 5,721,185, 5,425,872, 5,350,723, WO97-35893 (equivalent to U.S. Ser. No. 08/818,530, filed Mar. 14, 1997), and United States provisional application Ser. No. 60/054586, filed Sep. 15, 1997. The teachings of the foregoing patents, publications, equivalents, and provisional applications are hereby incorporated by reference thereto.

Combinations of strong Lewis acids, especially the combination of a trialkyl aluminum compound having from 1 to 4 carbons in each alkyl group and a halogenated tri (hydrocarbyl)boron compound having from 1 to 10 carbons in each hydrocarbyl group, especially tris (pentafluorophenyl)borane; further combinations of such strong Lewis acid mixtures with a polymeric or oligomeric alumoxane; and combinations of a single strong Lewis acid, especially tris(pentafluorophenyl)borane with a polymeric or oligomeric alumoxane are especially desirable activating cocatalysts.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis, are used such that electrolysis byproducts that would render the metal complex catalytically inactive are not substantially formed during the reaction. More particularly, suitable solvents are materials that are liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (ortho, meta, or para isomers), dimethoxyethane, and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, $A^-$. Preferred supporting electrolytes are salts corresponding to the formula $$G^+A^-$$

wherein:

$G^+$ is a cation which is nonreactive towards the starting and resulting complex; and $A^-$ is a noncoordinating, compatible anion.

Examples of cations, $G^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoro-aryl) borates having from 1 to 10 carbons in each hydrocarbyl group, especially tetra-n-butylammonium tetrakis(pentafluorophenyl) borate.

Suitable activating compounds useful as a cocatalyst in one embodiment of the present invention comprise a cation which is a Bronsted acid capable of donating a proton, and an inert, compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially. Therefore, said single boron atom compounds are preferred.

Preferably such cocatalysts may be represented by the following general formula:

$$(L^*\!\!-\!\!H)_d^+(A^{d-})$$

wherein:

$L^*$ is a neutral Lewis base;

$(L^*\!\!-\!\!H)+$ is a Bronsted acid;

$A^{d-}$ is a noncoordinating, compatible anion having a charge of d–, and d is an integer from 1 to 3.

More preferably $A^{d-}$ corresponds to the formula:

$$[M'^{k+}Q'_{n'}]^{d-}$$

wherein:

k is an integer from 1 to 3;

n' is an integer from 2 to 6;

n'–k=d;

M' is an element selected from Group 13 of the Periodic Table of the Elements; and Q' independently each occurrence is an hydride, dialkylamido, halide, alkoxide, aryloxide, hydrocarbyl, or halosubstituted-hydrocarbyl radical, said Q' having up to 20 carbons with the proviso that in not more than one occurrence is Q' halide.

In a more preferred embodiment, d is one, that is the counter ion has a single negative charge and corresponds to the formula $A^-$. Activating cocatalysts comprising boron which are particularly useful in the preparation of catalysts of this invention may be represented by the following general formula:

$$[L^*\!\!-\!\!H]^+[BQ''_4]^-$$

wherein:

$L^*$ is as previously defined;

B is boron in a valence state of 3; and

Q'' is a fluorinated $C_{1-20}$ hydrocarbyl group.

Most preferably, Q'' is in each occurrence a fluorinated aryl group, especially a pentafluorophenyl group.

Illustrative, but not limiting examples of boron compounds which may be used as an activating cocatalyst in the preparation of the improved catalysts of this invention are tri-substituted ammonium salts such as:

trimethylammonium tetrakis(pentafluorophenyl)borate, dimethylanilinium tetrakis(pentafluorophenyl)borate, dimethyltetradecylammonium tetrakis(pentafluorophenyl)borate, dimethyhexadecylammonium tetrakis(pentafluorophenyl)borate, dimethyloctadecylammonium tetrakis(pentafluorophenyl)borate, methylbis(tetradecyl)ammonium tetrakis(pentafluorophenyl)borate, methylbis(hexadecyl)ammonium tetrakis(pentafluorophenyl)borate, methylbis(octadecyl)ammonium tetrakis(pentafluorophenyl)borate, and mixtures thereof.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having a charge of e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$©^+A^-$$

wherein:

©+ is a $C_{1-20}$ carbenium ion; and $A^-$ is as previously defined. A preferred carbenium ion is the trityl cation, that is triphenylcarbenium.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:1000 to 1:1. In a particularly preferred embodiment of the invention the cocatalyst can be used in combination with a $C_{3-30}$ trihydrocarbyl aluminum compound, $C_{3-30}$ (hydrocarbyloxy) dihydrocarbylaluminum compound, or oligomeric or polymeric alumoxane. Which aluminum compounds are employed for their beneficial ability to scavenge impurities such as oxygen, water, and aldehydes from the polymerization mixture. Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, and methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The catalysts may exist as cationic derivatives of the dual metal center complexes, as zwitterionic derivatives thereof, or in an as yet undetermined relationship with the cocatalyst activator.

The catalysts may be used to polymerize ethylenically and/or acetylenically unsaturated monomers having from 2 to 20 carbon atoms either alone or in combination. Preferred monomers include the $C_{2-10}$ α-olefins especially ethylene, propylene, isobutylene, 1-butene, 1-hexene, 4-methyl-1-pentene, and 1-octene and mixtures thereof. Other preferred monomers include vinylcyclohexene, vinylcyclohexane, styrene, $C_{1-4}$ alkyl substituted styrene, tetrafluoroethylene, vinylbenzocyclobutane, ethylidenenorbornene and 1,4-hexadiene.

In general, the polymerization may be accomplished at conditions well known in the prior art for Ziegler-Natta or Kaminsky-Sinn type polymerization reactions, that is, temperatures from 0–250° C. and pressures from atmospheric to 3000 atmospheres. Suspension, solution, slurry, gas phase or high pressure, whether employed in batch or continuous form or under other process conditions, may be employed if desired. For example, the use of condensation in a gas phase polymerization is a especially desirable mode of operation for use of the present catalysts. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere, which teachings disclose conditions that can be employed with the polymerization catalysts of the present invention. A support, especially silica, alumina, or a polymer (especially polytetrafluoroethylene or a polyolefin) may be employed, and desirably is employed when the catalysts are used in a gas phase polymerization process with or without condensation. Methods for the preparation of supported catalysts are disclosed in numerous references, examples of which are U.S. Pat. Nos. 4,808,561, 4,912,075, 5,008,228, 4,914,253, and 5,086,025 and are suitable for the preparation of supported catalysts of the present invention.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents for solution, suspension, slurry or high pressure polymerization processes are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, butadiene, cyclopentene, 1-hexene, 3-methyl—1-pentene, 4-methyl-1-pentene, 1,4-hexadiene, 1-octene, 1-decene, styrene, divinylbenzene, allylbenzene, and vinyltoluene (including all isomers alone or in admixture). Mixtures of the foregoing are also suitable.

Having described the invention the following examples are provided as further illustration thereof and are not to be construed as limiting. Unless stated to the contrary all parts and percentages are expressed on a weight basis. The invention herein disclosed may be performed in the absence of any reagent not specifically described.

Tetrahydrofuran (THF), diethylether, toluene, and hexane were used following passage through double columns charged with activated alumina and Q-5® catalyst.

The compounds [1,3-Bis(diphenylphosphino)propane] dichloronickel(II), $MgCH_2Si(CH_3)_3$, n-BuLi, and pentamethylenebis(magnesium bromide) were all used as purchased from Aldrich. 2-bromoindene was prepared by dehydration of 2-bromoindanol and its identity confirmed by comparison to literature. All syntheses were performed under dry nitrogen or argon atmospheres using a combination of glove box and high vacuum techniques.

EXAMPLE 1

Titanium, dichloro(N-(1,1-dimethylethyl)-1-((1,2,3,3a,7a-η)-1H-inden-1-yl)-1,1-dimethylsilanaminato(2-)-N)(2,2'-(1,5-pentanediyl)bis-

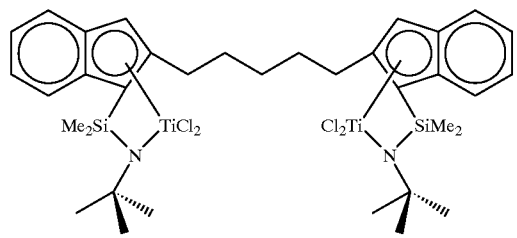

Preparation of pentamethylenebis(indene-2-yl).

2-Bromoindene (22.26 g, 114.1 mmol) and [1,3-bis(diphenylphosphino)-propane]dichloronickel (II) (0.523 g, 0.965 mmol) were stirred in diethylether (150 mL) at −78° C. as pentamethylenebis(magnesium bromide) (57.1 mmol, 114.1 mL of 0.5M solution in tetrahydrofuran (THF)) was added slowly. The dry ice bath was then removed and the mixture allowed to warm slowly to about 20° C. and then for two additional hours at room temperature. After the reaction period the mixture was then poured onto ice and washed with 1M HCl (1×100 mL), 1M $NaHCO_3$ (1×100 mL), and then $H_2O$ (1×100 mL). The organic fraction was then dried over $MgSO_4$, filtered, and the volatiles removed resulting in the isolation of a yellow oil. Recrystallization from methanol resulted in the isolation of the desired product as a white crystalline solid (7.23 g, 42.1 percent yield).

Preparation of pentamethylenebis(1-((t-butylamino) dimethylsilyl)indene-2-yl).

Pentamethylenebis(indene-2-yl) (3.001 g, 9.987 mmol) was stirred in THF (50 mL) as nBuLi (20.0 mmol, 10.00 mL of 2.0M solution in cyclohexane) was added slowly. This mixture was allowed to stir for 16 hours. This solution was then added dropwise to a solution of $ClSi(CH_3)_2NH$-t-Bu (3.501 g, 21.13 mmol) in THF (100 mL). This mixture was then allowed to stir for 16 hours. After the reaction period the volatiles were removed under vacuum and the residue extracted and filtered using toluene. Removal of the toluene under vacuum resulted in the isolation of the desired product as a pale yellow solid (4.827 g, 86.5 percent yield).

Preparation of tetralithio pentamethylenebis(1-((t-butylamido)dimethylsilyl)indene-2-yl)·4 THF Pentamethylenebis(1-((t-butylamino)dimethylsilyl) indene-2-yl) (3.182 g, 5.69 mmol) was stirred in THF (100 mL) as nBuLi (26.0 mmol, 13.00 mL of 2.0M solution in cyclohexane) was added slowly. This mixture was then allowed to stir overnight. After the reaction period the volatiles were removed and the residue washed well with hexane and dried under vacuum. The desired product was then isolated as a tan solid and used without further purification or analysis (4.749 g, 97.1 percent yield).

Preparation of titanium, dichloro(N-(1,1-dimethylethyl)-1-((1,2,3,3a,7a-η)-1H-inden-1-yl)-1,1-dimethylsilanaminato (2-)-N)(2,2'-(1,5-pentanediyl)bis- Tetralithio pentamethylenebis(1-((t-butylamido) dimethylsilyl)indene-2-yl)·4 THF (2.647 g, 3.081 mmol) in THF (50 mL) was added dropwise to a slurry of $TiCl_3$ $(THF)_3$ (2.809 g, 7.580 mmol) in THF (100 mL). This mixture was then allowed to stir for three hours. $PbCl_2$ (2.254 g, 8.104 mmol) was then added as a solid and the mixture allowed to stir for an additional hour. After the reaction period the volatiles were removed under vacuum and the residue extracted and filtered using toluene. The toluene was then removed under vacuum and the residue slurried in hexane/$CH_2Cl_2$ (100 mU25 mL), filtered, and dried under vacuum resulting in the isolation of the desired product as a red/brown microcrystalline solid (1.186 g, 48.6 percent yield).

EXAMPLE 2

Ttitanium, bis(trimethylsilvlmethyl)(N-(1,1-dimethylethyl)-1-((1,2,3,3a,7a-η)-1H-inden-1-yl)-1,1-dimethylsilanaminato(2-)-N)(2.2'-(1,5-pentanediyl)bis-

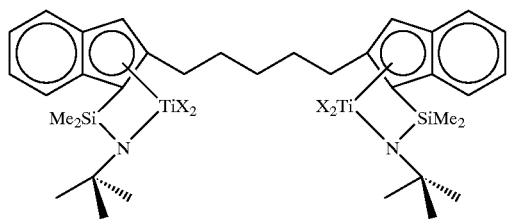

X=$CH_2Si(CH_3)_3$

Titanium, dichloro(N-(1,1-dimethylethyl)-1-((1,2,3,3a,7a-η)-1H-inden-1-yl)-1,1-dimethylsilanaminato(2-)-N)(2, 2'-(1,5-pentanediyl)bis- (0.934 g, 1.18 mmol) was stirred in diethylether (100 mL) as $MgCH_2Si(CH_3)_3$ (4.72 mmol, 4.72 mL of 1M solution in THF) was added dropwise. This mixture was allowed to stir overnight. After the reaction period the volatiles were removed under vacuum and the residue extracted and filtered using hexane. Removal of the hexane under vacuum resulted in the isolation of a gold solid (0.911 g, 77.3 percent yield).

Polymerization

A two liter reactor is charged with 750 g of Isopar E and 120 g of octene-1 comonomer. Hydrogen is added as a molecular weight control agent by differential pressure expansion from a 75 ml additional tank from 300 psig (2070 Kpa) to 275 psig (1890 Kpa). The reactor is heated to the polymerization temperature of 140° C. and saturated with ethylene at 500 psig (3450 Kpa). The appropriate amount of catalyst and cocatalyst as 0.005 M solutions in toluene (approximately 4 μmole) were premixed in a glovebox to give a 1:1 molar ratio of catalyst and cocatalyst, and transferred to a catalyst addition tank and injected into the reactor. The polymerization conditions were maintained for 10 minutes with ethylene on demand. The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos 168). Polymers formed are dried in a programmed vacuum oven with a maximum temperature of 120° C. and a 20 hours heating cycle. Results are shown in Table 1.

TABLE 1

| Run | complex | cocat. | Yield (g) | Eff.[1] | MI[2] | density[3] | Mw/Mn |
|---|---|---|---|---|---|---|---|
| 1 | Ex. 1 | MAO[4] | 18.4 | 47 | 2.42 | — | — |
| 2 | Ex. 1 | MAO[5] | 13.0 | 68 | 2.73 | — | — |
| 3 | Ex. 2 | FAB[6] | 10.6 | 28 | .70 | .881 | 2.3 |
| 4 | Ex. 2 | ATPFB[7] | 9.0 | 23 | .45 | .879 | 2.1 |

[1]efficiency Kg polymer/g Ti
[2]melt index, dg/min, measured by micromelt indexer
[3](g/cm$^3$)
[4]methylalumoxane
[5]methylalumoxane premixed with metal complex 15 minutes before addition to reactor
[6]tris(pentafluorophenyl)borane premixed with metalcomplex 20 minutes before addition to reactor
[7]dimethylanilinium tetrakis(pentafluorophenyl)borate premixed with metal complex 20 minutes before addition to reactor

EXAMPLE 3

Titanium, di(N,N-dimethylamido(N-(1,1-dimethylethyl)-1-((1,2,3,3a,7a-η)-H-inden-1-yl-1,1-dimethylsilanaminato (2-)-N)(3,3'-(1,2-ethanediyl)bis-

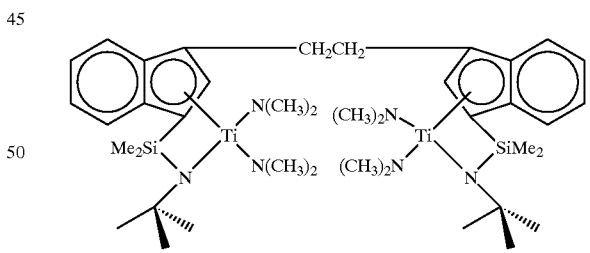

A) Synthesis of 1,2-ethanebis{3,3'-(dimethylchlorosilyl) inden-1-yl}

In a 250 mL flask, 1,2-bis(indenyl)ethane (10 g, 38.7 mmol) was dissolved in 150 mL dry THF and the stirring solution was cooled to −78° C. Next 52.3 mL of n-butyllithium (1.6 M in hexanes, 83.7 mmol) was then added dropwise by syringe. The solution turned brown and was allowed to warm slowly to room temperature overnight. The solution was then added slowly to a solution of $Me_2SiCl_2$ (25 mL) in 100 mL THF at −78° C. and the resulting mixture warmed up slowly to room temperature. All the volatiles were removed under vacuum and the product was extracted with pentane. An oily product was obtained after filtration and pentane removal under vacuum. Yield, 15 g (87 percent). The products are two isomers [(RR, SS) vs (RS, SR)] in a 1:1 ratio and were used without further purification. One isomer which has lower solubility in pentane was gradually precipitated out by removing the pentane very slowly over a period of one month. Spectroscopic and analytical data are as follows: Isomer I: $^1$H NMR ($C_6D_6$, 23° C.): δ 7.544 (d, 2H, $^3J_{H-H}$=8.0 Hz, Ind, $C_6H_4$), 7.372 (d, 2H, $^3J_{H-H}$=7.2 Hz, Ind, $C_6H_4$), 7.248 (dd, 2H, $^3J_{H-H}$=7.2 Hz, Ind, $C_6H_4$), 7.174 (dd, 2H, $^3J_{H-H}$=7.5 Hz, Ind, $C_6H_4$), 6.273 (s, 2H, Ind, $C_5H_2$), 3.482 (s, 2H, Ind, $C_5H_2$), 2.920 (br, s, 4H, $CH_2CH_2$), 0.041 (s, 6H, $SiMe_2$), −0.017 (s, 6H, $SiMe_2$). $^{13}$C NMR ($C_6D_6$, 23° C.): δ 144.967 (s, Ind), 144.003 (s, Ind), 143.897 (s, Ind), 127.887 (d, $^1J_{C-H}$=165.5 Hz, Ind), 126.015 (dd, $^1J_{C-H}$=158.1 Hz, $^2J_{C-H}$=6.3 Hz, Ind), 124.897 (dd, $J_{C-H}$=158.1 Hz, $2J_{C-H}$=6.9 Hz, Ind), 123.785 (dd, $^1J_{C-H}$=157.1 Hz, $^2J_{C-H}$=7.4 Hz, Ind), 119.675 (dd, $^1J_{C-H}$=157.1 Hz, $^2J_{C-H}$=8.0 Hz, Ind), 45.826 (dd, $^1J_{C-H}$=131.6 Hz, $^2J_{C-H}$=8.5 Hz, Ind), 27.043 (t, $^1J_{C-H}$=128.3 Hz, $CH_2CH_2$), −0.244 (q, $^1J_{C-H}$=121.6 Hz. $SiMe_2$), −0.342 (q, $^1J_{C-H}$=121.5 Hz, $SiMe_2$). Isomer II: $^1$H NMR ($C_6D_6$, 23° C.): δ 7.534 (d, 2H, Ind, $C_6H_4$), 7.352 (d, 2H, Ind, $C_6H_4$), 7.241 (dd, 2H, $^3J_{H-H}$=7.5 Hz, Ind, $C_6H_4$), 7.168 (dd, 2H, Ind, $C_6H_4$), 6.31 (s, 2 H, Ind, $C_5H_2$), 3.49 (s, 2H, Ind, $C_5H_2$), 2.91 (br, s, 4H, $CH_2CH_2$), 0.064 (s, 6H, SiMe2), −0.014 (s, 6H, $SiMe_2$). $^{13}$C NMR ($C_6D_6$, 23° C.): δ 144.975 (s, Ind), 144.060 (s, Ind), 143.920 (s, Ind), 127.944 (d, $^1J_{C-H}$=165.5 Hz, Ind), 126.029 (dd, $^1J_{C-H}$=158.1 Hz, $^2J_{C-H}$=6.3 Hz, Ind), 124.903 (dd, $^1J_{C-H}$=158.1 Hz, $^2J_{C-H}$=6.9 Hz, Ind), 123.791 (dd, $^1J_{C-H}$=157.1 Hz, $^2J_{C-H}$=7.4 Hz, Ind), 119.695 (dd, $^1J_{C-H}$=157.1 Hz, $^2J_{C-H}$=8.0 Hz, Ind), 45.868 (dd, $^1J_{C-H}$=130.6 Hz, $^2J_{C-H}$=8.4 Hz, Ind), 27119 (t, $J_{C-H}$=127.4 Hz, $CH_2CH_2$), −0.202 (q, $^1J_{C-H}$=122.1 Hz. $SiMe_2$), −0.315 (q, $^1J_{C-H}$=122.1 Hz, $SiMe_2$).

B) Synthesis of 1,2-ethanebis{3,3'-((dimethyl)(t-butylamino)silyl)inden-1-yl}

1,2-ethanebis{3,3'-(dimethylchlorosilyl)inden-1-yl} (15 g, 33.8 mmol) was dissolved with THF (150 mL) in a 250 mL flask and the stirring solution was cooled to 0° C. Bu$^t$NH (16.3 mL, 154.8 mmol) was then added dropwise by syringe. A white precipitate formed immediately. The solution was stirred at room temperature overnight. All the volatiles were then removed under vacuum and the product was extracted with pentane. Orange oily product was obtained after filtration and pentane removal under vacuum. The products were two isomers [(RR, SS) vs (RS, SR)] in a 1:1 ratio. The product was used to synthesize bimetallic complexes without further purification. Yield, 14.2 g (91 percent). Spectroscopic and analytical data for the mixture are as follows. $^1$H NMR ($C_6D_6$, 23° C.): δ 7.636–7.231 (m, 16H, Ind, $C_6H_4$), 6.496 (s, 2H, Ind, $C_5H_2$), 6.461 (s, 2H, Ind, $C_5H_2$), 3.477 (s, 4H, Ind, $C_5H_2$), 3.165 (br, s, 8H, $CH_2CH_2$), 1.067 (s, 32H, $NCMe_3$), 0.491 (br, 4H, NH), 0.002 (s, 6H, $SiMe_2$), −0.025 (s, 6H, $SiMe_2$), −0.054 (s, 12H, $SiMe_2$). $^{13}$C NMR ($C_6D_6$, 23° C.): δ 146.830 (s, Ind), 145.507 (s, Ind), 145.464 (s, Ind), 142.297 (s, Ind), 142.199 (s, Ind), 131.093 (d, $^1J_{C-H}$=164.6 Hz, Ind), 125.406 (dd, $^1J_{C-H}$=159.2 Hz, $^2J_{C-H}$=7.4 Hz, Ind), 124.376 (dd, $^1J_{C-H}$=158.2 Hz, $^2J_{C-H}$=7.5 Hz, Ind), 123.900 (dd, $^1J_{C-H}$=155.0 Hz, $^2J_{C-H}$=6.4 Hz, Ind), 119.776 (dd, $J_{C-H}$=158.1 Hz, $2J_{C-H}$=7.5 Hz, Ind), 49.833 (s, $NCMe_3$), 47.497 (dd, $^1J_{C-H}$=127.4 Hz, $^2J_{C-H}$=7.5 Hz, Ind), 34.195), 34.195 (t, $^1J_{C-H}$=128.3 Hz, $NCMe_3$), 28.114 (t, $^1J_{C-H}$=127.9 Hz, $CH_2CH_2$), 27.946 (t, $^1J_{C-H}$=127.9 Hz, $CH_2CH_2$), 0.512 (q, $^1J_{C-H}$=118.9 Hz. $SiMe_2$), 0.456 (q, $^1J_{C-H}$=118.9 Hz. $SiMe_2$), −0.248 (q, $^1J_{C-H}$=118.9 Hz, $SiMe_2$).

C) Titanium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis- 1,2-ethanebis{3,3'-((dimethyl)(t-butylamino)silyl)inden-1-yl} (5.76 g, 11.2 mmol) was dissolved with 35 mL pentane in a 250 mL flask. A solution of Ti(NMe$_2$)$_4$ (5.0 g, 22.3 mmol) in 100 mL toluene was then added. The mixture was refluxed at 110° C. for 30 h with slow but constant $N_2$ purging to remove HNMe$_2$. The concentrated solution was then cooled slowly to 0° C. to yield red crystals. The product was purified by recrystallization from toluene and washing with pentane. Yield 4.3 g (49 percetn). Spectroscopic and analytical data for the product are as follows. $^1$H NMR ($C_6D_6$, 23° C.): δ 7.906 (d, 2H, $^3J_{H-H}$=8.7 Hz, Ind, $C_6H_4$), 7.585 (d, 2 H, $^3J_{H-H}$=8.0 Hz, Ind, $C_6H_4$), 7.020 (dd, 2H, $^3J_{H-H}$=7.6 Hz, $J_{H-H}$=7.0 Hz, Ind, $C_6H_4$), 6.905 (dd, 2H, $^3J_{H-H}$=8.4 Hz, $^3J_{H-H}$=6.6 Hz, Ind, $C_6H_4$), 6.333 (s, 2H, Ind, $C_5H$), 3.450–3.364 (m, 4H, $CH_2CH_2$), 3.027 (s, 12H, $TiNMe_2$), 2.350 (s, 12H, $TiNMe_2$), 1.240 (s, 18H, $NCMe_3$), 0.852 (s, 6H, $SiMe_2$), 0.643 (s, 6H, $SiMe_2$). $^{13}$C NMR ($C_6D_6$, 23° C.): δ 133.471 (Ind), 131.171 (Ind), 126.160 (Ind), 126.026 (Ind), 124.240 (Ind), 123.810 (Ind), 122.021 (Ind), 121.571 (Ind), 91.058 (Ind), 60.428 ($NCMe_3$), 49.526 ($TiNMe_2$), 47.816 ($TiNMe_2$), 34.204 ($NCMe_3$), 30.222 ($CH_2CH_2$), 5.155 ($SiMe_2$), 2.998 ($SiMe_2$). Anal. Calcd for $C_{40}H_{68}N_6Si_2Ti_2$: C, 61.20; H, 8.73; N, 10.71. Found: C, 61.41; H, 8.60; N, 10.71.

EXAMPLE 4

Titanium, dimethyl(N-(1,1-dimethylethyl)-1-((1,2,3,3a,7a-η)-1H-inden-1-yl)-1,1-dimethylsilanaminato(2-)-N)(3.3'-(1,2-ethanediyl)bis-

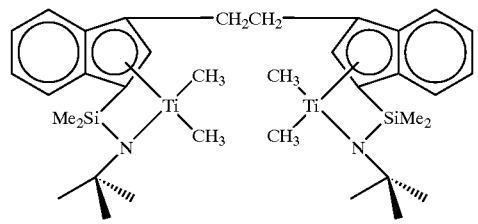

Titanium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis-(from Example 3) (800 mg, 1.02 mmol) was dissolved with 100 mL toluene in a 250 mL flask. A solution of AlMe$_3$ (5.0 mL, 2.0M in hexanes) was added slowly by syringe at room temperature. The solution first turned yellow and then cloudy during the addition. The solution was stirred at room temperature for two days. All the volatiles were removed by vacuum and the yellow solid product was purified by washing with pentane at room temperature. Yield, 607 mg (89 percent). Spectroscopic and analytical data are as follows. $^1$H NMR ($C_6D_6$, 23° C.): δ 7.492 (d, 2H, $^3J_{H-H}$=8.7 Hz, Ind, $C_6H_4$), 7.463 (d, 2H, $^3J_{H-H}$=8.7 Hz, Ind, $C_6H_4$), 7.115–7.066 (m, 2H, Ind, $C_6H_4$), 6.928 (m, 2H, Ind, $C_6H_4$), 5.997 (s, 2H, Ind, $C_5H$), 3.443–3.305 (m, 4H, $CH_2CH_2$), 1.457 (s, 18H, $NCMe_3$), 0.766 (s, 6H, $SiMe_2$), 0.569 (s, 6H, $SiMe_2$), 0.352 (s, 6H, $TiMe_2$), −0.111 (s, 6H, $TiMe_2$). $^{13}$C NMR ($C_6D_6$, 23° C.): δ 134.264 (Ind), 132.596 (Ind), 127.782 (Ind), 126.367 (Ind), 126.072 (Ind), 125.755 (Ind), 125.438 (Ind), 124.073 (Ind), 90.165 (Ind), 58.623 ($NCMe_3$), 56.525 ($TiMe_2$), 56.061 ($TiMe_2$), 34.462 ($NCMe_3$), 30.120 ($CH_2CH_2$), 4.010 ($SiMe_2$), 1.906 ($SiMe_2$). Anal. Calcd for $C_{36}H_{56}N_2Si_2Ti_2$: C, 64.65; H, 8.44; N, 4.19. Found: C, 63.65; H, 8.38; N, 4.10.

EXAMPLE 5
Zirconium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis-

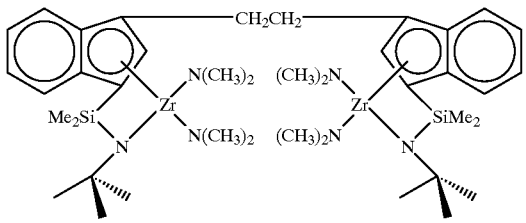

1,2-Ethanebis{3,3'-((dimethyl)(t-butylamino)silyl)inden-1-yl} (5.0 g, 9.67 mmol) was dissolved with 35 mL pentane in a 250 mL flask. A solution of $Zr(NMe_2)_4$ (5.2 g, 19.4 mmol) in 100 mL toluene was then added. The mixture was refluxed at 110° C. for 8 h with slow but constant $N_2$ purging to remove $HNMe_2$. The concentrated solution was then cooled down slowly to 0° C. to yield light yellow crystals. The product was purified by recrystallization from toluene and washing with pentane. Yield, 5.6 g (66 percent). Spectroscopic and analytical data are as follows. $^1H$ NMR ($C_6D_6$, 23° C.): δ 7.90–7.86 (m, 2H, Ind, $C_6H_4$), 7.55–7.49 (m, 2H, Ind, $C_6H_4$), 7.02–6.90 (m, 4H, Ind, $C_6H_4$), 6.52 (s, 2H, Ind, $C_5H$), 6.50 (s, 2H, Ind, $C_5H$), 3.34 (br, s, 4H, $CH_2CH_2$), 2.88 (s, 6H, $ZrNMe_2$), 2.87 (s, 6H, $ZrNMe_2$), 2.22 (s, 6H, $ZrNMe_2$), 2.21 (s, 6H, $ZrNMe_2$), 1.24 (s, 9H, $NCMe_3$), 1.23 (s, 9H, $NCMe_3$), 0.86 (s, 6H, $SiMe_2$), 0.67 (s, 6H, $SiMe_2$). $^{13}C$ NMR ($C_6D_6$, 23° C.): δ 133.39 (Ind), 129.46 (Ind), 125.48 (Ind), 124.05 (Ind), 123.72 (Ind), 123.70 (Ind), 121.85 (Ind), 121.79 (Ind), 121.58 (Ind), 121.43 (Ind), 90.88 (Ind), 90.80 (Ind), 56.38 ($NCMe_3$), 44.57 ($ZrNMe_2$), 44.53 ($ZrNMe_2$), 42.39 ($ZrNMe_2$), 34.58 ($NCMe_3$), 29.58 ($CH_2CH_2$), 29.43 ($CH_2CH_2$), 5.85 ($SiMe_2$), 3.51 ($SiMe_2$). Anal. Calcd for $C_{40}H68N_6Si_2Zr_2$: C, 55.12; H, 7.86; N, 9.64. Found: C, 54.97; H, 7.91; N, 9.63.

EXAMPLE 6
Zirconium, dimethyl(N-(1,1-dimethylethyl)-1-((1,2,3,3a,7a-η)-1H-inden-1-yl)-1,1-dimethylsilanaminato(2-)-N)(3,3'-(1,2-ethanediyl)bis-

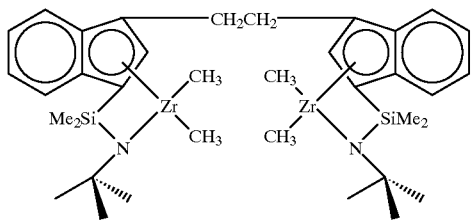

Zirconium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis- (from Example 5) (800 mg, 0.92 mmol) was dissolved with 100 mL toluene in a 250 mL flask. A solution of $AlMe_3$ (5.0 mL, 2.0M in hexanes) was added slowly by syringe at room temperature. The solution first turned yellow and then cloudy during the addition. The solution was stirred at room temperature for another 4 h. All the volatiles were removed under vacuum, and the white solid product was purified by washing with pentane at room temperature. Yield, 587 mg (84 percent). Spectroscopic and analytical data are as follows. $^1H$ NMR ($C_6D_6$, 23° C.): δ 7.594 (d, 2H, $^3J_{H-H}$=8.7 Hz, Ind, $C_6H_4$), 7.362 (d, 2H, $^3J_{H-H}$=7.2 Hz, Ind, $C_6H_4$), 7.028 (dd, 2H, $^3J_{H-H}$=7.5 Hz, $^3J_{H-H}$=6.7 Hz, Ind, $C_6H_4$), 6.918 (dd, 2H, $^3J_{H-H}$=8.4 Hz, $^3J_{H-H}$=6.7 Hz, Ind, $C_6H_4$), 6.259 (s, 2H, Ind, $C_5H$), 3.238 (br, s, 4H, $CH_2CH_2$), 1.308 (s, 18H, $NCMe_3$), 0.621 (s, 6H, $SiMe_2$), 0.406 (s, 6H, $SiMe_2$), 0.181 (s, 6H, $ZrMe_2$), –0.715 (s, 6H, $ZrMe_2$). $^{13}C$ NMR ($C_6D_6$, 23° C.): δ 133.644 (Ind), 130.069 (Ind), 126.072 (Ind), 125.410 (Ind), 125.157 (Ind), 124.875 (Ind), 123.454 (Ind), 122.961 (Ind), 86.726 (Ind), 55.403 ($NCMe_3$), 40.680 ($ZrMe_2$), 39.160 ($ZrMe_2$), 34.305 ($NCMe_3$), 29.660 ($CH_2CH_2$), 4.473 ($SiMe_2$), 2.665 ($SiMe_2$). Anal. Calcd for $C_{36}H_{56}N_2Si_2Zr_2$: C, 57.24; H, 7.47; N, 3.71. Found: C, 56.90; H, 7.43; N, 3.65.

Ethylene Polymerization Experiments

On a high vacuum line ($10^{-5}$ torr), ethylene polymerizations were carried out in 250 mL round-bottom three-neck flasks equipped with a magnetic stirring bar and a thermocouple probe. In a typical experiment, dry toluene (100 mL) was vacuum-transferred into the flask, pre-saturated under 1.0 atm of rigorously purified ethylene (pressure control using a mercury bubbler), and equilibrated at the desired reaction temperature using an external bath. The catalytically active species were freshly generated using a solution having a 1:2 metallocene:cocatalyst mole ratio in 1.5 mL of toluene. The solution of catalyst was then quickly injected into the rapidly stirred flask using a gas-tight syringe equipped with a spraying needle. The temperature of the toluene solution in representative polymerization experiments was monitored using a thermocouple (OMEGA Type K thermocouple with a Model HH21 microprocessor thermometer). The reaction exotherm temperature rise was invariably less than 5° C. during these polymerizations. After a measured time interval (short to minimize mass transport and exotherm effects), the polymerization was quenched by the addition of 15 mL 2 percent acidified methanol. Another 100 mL methanol was then added and the polymer was collected by filtration, washed with methanol, and dried on the high vacuum line overnight to a constant weight.

Results are shown in Table 2.

TABLE 2

| Run | complex (mM) | time (min) | temp ° C. | cocat. | Yield (g) | Eff.[1] | Tm[2] (° C.) |
|---|---|---|---|---|---|---|---|
| 1 | Ex. 4 (0.1) | 60 | 80 | TCTPB[3] | 23.5 | 2.4 | — |
| 2 | Ex. 4 (0.1) | 60 | 23 | TCTPB[4] | 0.27 | 0.03 | — |
| 3 | Ex. 2 (0.1) | 4 | 90 | BPFB[5] | 0.85 | 1.3 | 134.1 |
| 4 | " | 3 | " | FAB[4] | 1.23 | 2.5 | 132.5 |
| 5 | " | 30 | 100 | " | 0.25 | 0.05 | 132.7 |
| 6 | " | 3 | 95 | " | 0.35 | 0.53 | 133.4 |

[1]efficiency Kg of polymer/[(mole of metal complex) · atm · h].
[2]polymer melting transition temperature
[3]triphenylcarbeniumtetrakis(pentafluorophenyl)borate ($Ph_3C^+$ [$B(C_6F_5)_4$]$^-$
[4]1,4-tetrafluorophenylene-bis{bis(pentafluorophenyl)borane} ([1,4-($B(C_6F_5)_2)_2](C_6F_4$))
[5]trispentafluorophenylborane

What is claimed is:

1. A bimetallic complex corresponding to the formula:

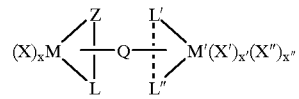

wherein:

M and M' are independently Group 3, 4, 5, 6, or Lanthanide metals;

L is a divalent group (or trivalent group if bound to Q) having up to 50 nonhydrogen atoms and containing an aromatic π-system through which the group is bound to M, said L also being bound to Z;

L' is a monovalent group or a divalent group (if bound to L' or Q), or a trivalent group if bound to both L' and Q) having up to 50 nonhydrogen atoms and containing an aromatic c-system through which the group is bound to M';

L" is a monovalent group or a divalent group (if bound to L' or Q), or a trivalent group if bound to both L' and Q) having up to 50 nonhydrogen atoms and containing an aromatic π-system through which the group is bound to M', or L" is a moiety comprising boron or a member of Group 14 of the Periodic Table of the Elements, and optionally also comprising nitrogen, phosphorus, sulfur or oxygen, said L' having up to 20 non-hydrogen atoms;

Z is a moiety comprising boron or a member of Group 14 of the Periodic Table of the Elements, and optionally also comprising nitrogen, phosphorus, sulfur or oxygen, said Z having up to 20 non-hydrogen atoms;

X and X' independently each occurrence are anionic ligand groups having up to 40 atoms exclusive of the class of ligands containing an aromatic π-system through which the group is bound to M or M', or optionally two X groups or two X' groups together form a $C_{4-40}$ conjugated or nonconjugated diene optionally substituted with one or more hydrocarbyl, silyl, halocarbyl, or halohydrocarbyl groups;

X" independently each occurrence is a neutral ligating compound having up to 20 atoms;

Q is a divalent anionic ligand group bound at one terminus to either Z or L and bound at the remaining terminus to either L' or L", said Q having up to 20 nonhydrogen atoms;

x and x' are independently integers from 0 to 3, selected to provide charge balance; and x" is a number from 0 to 3.

2. A bimetallic complex according to claim 1 corresponding to the formula:

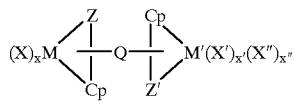

wherein Z, M, M', X, X', x and x' are as previously defined in claim 1;

Z' is a moiety comprising boron or a member of Group 14 of the Periodic Table of the Elements, and optionally also comprising nitrogen, phosphorus, sulfur or oxygen, said Z' having up to 20 non-hydrogen atoms;

Cp and Cp' are cyclic $C_5R'_4$ groups bound to Z or Z' respectively and bound to M or M' respectively by means of delocalized π-electrons, wherein R', independently each occurrence, is hydrogen, hydrocarbyl, silyl, halo, fluorohydrocarbyl, hydrocarbyloxy, hydrocarbylsiloxy, N,N-di(hydrocarbylsilyl)amino, N-hydrocarbyl-N-silylamino, N,N-di(hydrocarbyl) amino, hydrocarbyleneamino, di(hydrocarbyl) phosphino, hydrocarbylsulfido; or hydrocarbyloxy-substituted hydrocarbyl, said R' having up to 20 nonhydrogen atoms, and optionally, two such R' substituents may be joined together thereby causing Cp or Cp' to have a fused ring structure, or further optionally, Cp or Cp' each independently is a trivalent derivative of the above identified $C_5R'_4$ group that is also bonded to Q and one R' on each of Cp or Cp' is a covalent bond to Q;

Q is a linear or cyclic hydrocarbylene, or silane group or a nitrogen, oxygen, or halo substituted derivative thereof, said Q having up to 20 nonhydrogen atoms.

3. A bimetallic complex according to claim 2 corresponding to the formula:

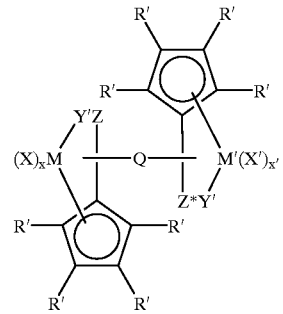

wherein:

M' is Ti, Zr, Hf, Sc, yittrium, or La;

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

Z and Z' independently each occurrence are —Z*Y'—, wherein:

Y' is —O—, —S—, —NR"—, —PR"—, —OR", or —NR"$_2$ (and with respect to —OR" and —NR"$_2$, one bond is a dative bond through the available electron pair), wherein R" is hydrogen, hydrocarbyl, silyl, or silylhydrocarbyl of up to 12 nonhydrogen atoms, or R" is a covalent bond to Q, and Z* is SiR*$_2$, CR*$_2$, SiR*$_2$SiR*$_2$, CR*$_2$CR*$_2$, CR*=CR*, CR*$_2$SiR*$_2$, or GeR*$_2$;

wherein R* each occurrence is independently hydrogen, hydrocarbyl, silyl, halogenated alkyl, or halogenated aryl, said R* having up to 12 non-hydrogen atoms.

4. A bimetallic complex according to claim 3 corresponding to the formula:

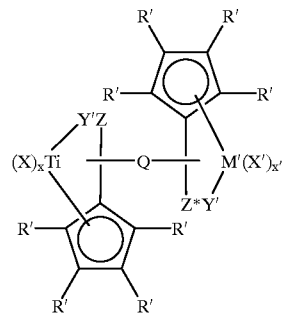

wherein:

Q is a linear or cyclic hydrocarbylene, silane group or a nitrogen or oxygen containing substituent thereof, R' is as previously defined in claim 3;
X and X' are $C_{1-10}$ hydrocarbyl; and
Y'Z* is: —NR"—(ER''')$_m$—
wherein:
E is independently each occurrence silicon or carbon;
R" is $C_{1-10}$ hydrocarbyl or a covalent bond to Q;
R''' is $C_{1-4}$ alkyl; and
m is an integer from 1 to 10.

5. A bimetallic complex according to claim 1 corresponding to the formula:

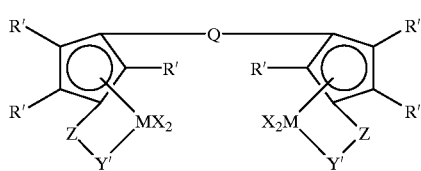

(I)

wherein:
M independently each occurrence is titanium or zirconium;
R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure,
Z independently each occurrence is $SiR*_2$, $CR*_2$, $SiR*_2SiR*_2$, $CR*_2CR*_2$, $CR*=CR*$, $CR*_2SiR*_2$, or $GeR*_2$; wherein R* each occurrence is independently hydrogen, hydrocarbyl, silyl, halogenated alkyl, or halogenated aryl, said R* having up to 12 nonhydrogen atoms;
Y' is —O—, —S—, —NR"—, or —PR, wherein R" is hydrogen, hydrocarbyl, silyl, or silylhydrocarbyl of up to 12 nonhydrogen atoms; and
X independently each occurrence is an anionic ligand group having up to 40 atoms exclusive of the class of ligands containing an aromatic π-system through which the group is bound to M, or optionally two X groups together form a $C_{4-40}$ conjugated or nonconjugated diene optionally substituted with one or more hydrocarbyl, silyl, halocarbyl, or halohydrocarbyl groups; and
Q is a divalent anionic ligand group having up to 20 nonhydrogen atoms.

6. A bimetallic complex according to claim 5 wherein:
Q is a linear or cyclic hydrocarbylene or silane group of up to 20 atoms other than hydrogen;
R' is hydrogen, $C_{1-20}$ hydrocarbyl, or two adjacent R' groups are joined together forming part of a fused ring system;
X is chloride, NR"$_2$, or R"; wherein R" is $C_{1-10}$ hydrocarbyl; and
Y'Z is: —NR"—(ER''')$_m$—, wherein:
E is independently each occurrence silicon or carbon;
R" is $C_{1-10}$ hydrocarbyl;
R''' is $C_{1-4}$ alkyl; and
m is an integer from 1 to 10.

7. A bimetallic complex according to claim 6 wherein:
M in both occurrences is titanium or zirconium;
Q is 1,2-ethanediyl;
the unsaturated ring system is cyclopentadienyl or indenyl;
X is chloride, N,N-dimethylamido or methyl; and
Y'Z is: dimethyl(t-butylamido)silane.

8. A bimetallic complex according to claim 1 which is, titanium, dichloro(N-(1,1-dimethylethyl)-1-((1,2,3,3a,7a-η)-1H-inden-1-yl)-1,1-dimethylsilanaminato(2-)-N)(2,2'-(1,5-pentanediyl)bis-, titanium, bis(trimethylsilylmethyl)(N-(1,1-dimethylethyl)-1-((1,2,3,3a,7a-η)-1H-inden-1-yl)-1,1-dimethylsilanaminato(2-)-N)(2,2'-(1,5-pentanediyl)bis-, zirconium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis-, zirconium, dimethyl(N-(1,1-dimethylethyl)-1-((1,2,3,3a,7a-η)-1H-inden-1-yl)-1,1-dimethylsilanaminato(2-)-N)(3,3'-(1,2-ethanediyl)bis-, titanium, di(N,N-dimethylamido)(N-(1,1-dimethylethyl)-1-((1,2,3,3a,7a-η)-1H-inden-1-yl)-1,1-dimethylsilanaminato(2-)-N)(3,3'-(1,2-ethanediyl)bis-, or titanium, dimethyl(N-(1,1-dimethylethyl)-1-((1,2,3,3a,7a-η)-1H-inden-1-yl)-1,1-dimethylsilanaminato(2-)-N)(3,3'-(1,2-ethanediyl)bis-.

9. In a process for the coordination polymerization of polymerizable monomers the improvement wherein the catalyst comprises a bimetallic complex according to any one of claims 1 to 8 and an activating cocatalyst.

* * * * *